(12) United States Patent
Köhler et al.

(10) Patent No.: US 6,168,700 B1
(45) Date of Patent: Jan. 2, 2001

(54) SENSOR FOR DETERMINING THE CONCENTRATION OF OXIDIZABLE CONSTITUENTS IN A GAS MIXTURE

(75) Inventors: Thomas Köhler, Stuttgart; Bernd Schumann, Rutesheim, both of (DE)

(73) Assignee: Robert Bosch GmbH, Stuttgart (DE)

( * ) Notice: Under 35 U.S.C. 154(b), the term of this patent shall be extended for 0 days.

(21) Appl. No.: 09/101,648

(22) PCT Filed: Oct. 27, 1997

(86) PCT No.: PCT/DE97/02490

§ 371 Date: Sep. 22, 1998

§ 102(e) Date: Sep. 22, 1998

(87) PCT Pub. No.: WO98/22812

PCT Pub. Date: May 28, 1998

(30) Foreign Application Priority Data

Nov. 15, 1996 (DE) ................................................ 196 47 268

(51) Int. Cl.[7] .................................................. G01N 27/407
(52) U.S. Cl. ......................... 204/427; 204/424; 204/426; 204/429; 205/787
(58) Field of Search ..................... 204/421–429

(56) References Cited

U.S. PATENT DOCUMENTS

| | | |
|---|---|---|
| 3,849,282 | 11/1974 | Degueldre et al. . |
| 5,393,397 | * 2/1995 | Fukaya et al. ........................ 204/425 |
| 5,522,979 | 6/1996 | Tatumoto et al. . |
| 5,643,429 | * 7/1997 | Wachsman ........................... 204/421 |

FOREIGN PATENT DOCUMENTS

| | | |
|---|---|---|
| 23 34 044 | 1/1974 | (DE) . |
| 42 44 723 | 3/1994 | (DE) . |
| 60-61654 | 4/1985 | (JP) . |

* cited by examiner

*Primary Examiner*—T. Tung
(74) *Attorney, Agent, or Firm*—Kenyon & Kenyon

(57) ABSTRACT

A sensor serves to determine the concentration of oxidizable components in a gas mixture, in particular for determining saturated and unsaturated hydrocarbons by measuring the voltage between at least one measuring electrode and a reference electrode. The material for the measuring electrode is based on compounds of the eschynite class, including eschynites, euxenites and samarskites with general formula $AB_2O_6$, which have the general empirical formula $A_{1-x}B_{2-y}B'_y(O,OH,F)_{6\pm z}$ and may be partially doped or may have occupancy defects.

12 Claims, 1 Drawing Sheet

SENSOR FOR DETERMINING THE CONCENTRATION OF OXIDIZABLE CONSTITUENTS IN A GAS MIXTURE

FIELD OF THE INVENTION

The present invention relates to a sensor for determining the concentration of oxidizable components in a gas mixture, in particular for determining saturated and unsaturated hydrocarbons.

BACKGROUND INFORMATION

Formula $A_{2-x}A'_xBO_4$ are described in German Patent No. 23 34 044. They are used for detecting oxidizable gases. It is also described in German Patent No. 42 44 723 that cuprates of rare earths of the formula $A_{2-x}L_xCuO_4$ can be used to detect oxygen in gas mixtures, in particular in exhaust gases from internal combustion engines and combustion systems. However, it has proven difficult so far to find suitable materials for determining saturated and unsaturated hydrocarbons. This is due to the low corrosion resistance of the electrode materials used, which have so far had a high tendency to form interfering sulfates on the electrode surface. The only relatively satisfactory option available so far is described in Japanese Patent No. 60 61 654, where hydrocarbons can be determined on metallic measuring electrodes of platinum.

SUMMARY OF THE INVENTION

A sensor according to the present invention is composed of a material of the general formula $AB_2O_6$ for the measuring electrode, i.e., materials from the class of eschynites in the narrower sense, which are also known as titanium niobates of the rare earths according to their most common representatives, samarskites, which are also known as yttrocolumbites, and euxenites, have a very high corrosion resistance at high temperatures and a low tendency to form sulfates. Due to the possible structural variations of the class of compounds referred to below in general as eschynites, it is possible to make available appropriate combinations of metals for A and B in the $AB_2O_6$ structures for various gases to be determined. In addition, this great structural variety permits the corresponding octahedral positions in the $AB_2O_6$ structure to be doped with a plurality of cations of comparable ionic radii if necessary.

A special advantage of the sensor according to the present invention is the use of natural eschynites as measuring electrodes, e.g., samarskite wiikite, yttrotantalite and clopinite which occur frequently in such deposits and are easily extracted. This leads to inexpensive application of eschynites which can be varied as needed.

For a specific application, however, it is also possible to synthesize the corresponding compounds with the desired stoichiometry easily and on a large scale in an especially advantageous manner, e.g., by the generally known method of hydrothermal synthesis at a low temperature and low pressure or by high temperature synthesis in quartz ampules. Hydrothermal synthesis first yields compounds in the eschynite phase, which at higher temperatures are converted monotropically to the high temperature euxenite phase.

In an especially preferred exemplary embodiment according to the present invention, item B of the mixed metal oxides of the eschynite family is at least partially replaced by transition metals. These are selected from the platinum metals, i.e., metals of the group ruthenium, rhodium, palladium, osmium, iridium and platinum, the coinage metals copper, silver, gold, and the iron group metals, i.e., iron, cobalt and nickel, as well as rhenium or transition metals in an oxidation state of +5. Compounds with nickel doping have proven especially advantageous. B of the eschynite is replaced by $Ni^{2+}$ cations in an amount of 0.005 to 0.2 mol %. This increases the sensitivity to hydrocarbons, as well as the electric conductivity of eschynites doped in this way.

In another preferred exemplary embodiment, oxygen in the $AB_2O_6$ structure may be partially replaced by hydroxide or fluoride anions, which causes a greater thermodynamic and kinetic stability while also yielding an improved electric conductivity of the material.

Another preferred exemplary embodiment uses an eschynite which is also deficient in A ($A_{1-x}$), i.e., has an occupancy defect. This measure also greatly improves the electric conductivity of the eschynite. Therefore, in a preferred general embodiment, the structural formula of eschynite can be given as $$A_{1-x}B_{2-y}B'_y(O,Oh,F)_{6\pm z}$$

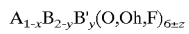

The thickness of the eschynite measuring electrode is preferably 5 to 100 micrometers, but preferably 20 to 30 micrometers, and the eschynite measuring electrode can be applied using a conventional method, preferably by a thick-film method.

In a preferred exemplary embodiment, the sensor is composed of various layers, i.e., a reference electrode made of platinum, for example, is applied to a flat, electrically insulating substrate, e.g., made of aluminum oxide, with a layer of ion-conducting solid electrolytes and the eschynite measuring electrode above that.

In an advantageous exemplary embodiment, the above sensor is used to determine saturated and unsaturated hydrocarbons in combustion exhaust gases. The layered structure of the sensor permits a high degree of miniaturization and therefore simplifies the design and also permits inexpensive manufacture because the solid electrolyte is sintered to become porous. This eliminates the need for a reference gas, which greatly simplifies probe design.

DETAILED DESCRIPTION OF THE INVENTION

Figure 1:
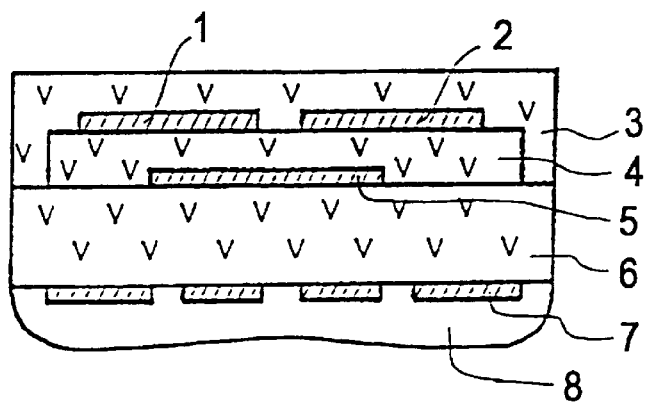
FIG. 1 shows a section through a sensor according to the present invention.

FIG. 1 shows a sectional view of a sensor according to the present invention. A planar, ceramic, electrically insulating substrate 6, such as aluminum oxide, has on one large surface superimposed layers of a reference electrode 5 of platinum, for example, a solid electrolyte 4, measuring electrodes 1 and 2 and a gas-permeable protective layer 3. A heater device 7 with a cover 8 is applied to the opposite large surface of the substrate.

To determine the concentration of oxidizable components in exhaust gases, the sensor is heated by heater device 7 to a temperature between 300° C. and 1000° C., preferably to approximately 600° C. To permit diffusion of the gas to be analyzed to the reference electrode and establishment of the oxygen equilibrium potential, the solid electrolyte may be sintered to become porous, but those skilled in the art may also select other options with which they are familiar, such as passing the gas over a reference channel or introducing a reference gas atmosphere.

The sensor generates a cell voltage over the oxygen ion-conducting solid electrolyte by a first half-cell reaction established with the help of the reference electrode and a second half-cell reaction on at least one measuring electrode, influenced by the oxidizable gas component to be determined. The concentration of the gas components is determined from the voltage values by using calibration curves. Thus in the simplest case, the sensor according to the present invention can be used with one reference electrode which catalyzes the establishment of an equilibrium in the gas mixture and with one measuring electrode which has little or no ability to catalyze the establishment of an equilibrium in the gas mixture. However, it is also possible to apply two measuring electrodes, as shown in FIG. 1, or multiple measuring electrodes, each with a different catalytic activity to establish oxygen equilibrium states. The measuring electrodes then respond with different voltages, depending on the type of gas, based on the reference electrode.

In another exemplary embodiment, the solid electrolyte is doped with foreign atoms, e.g., with 0.01 to 10 vol% added platinum. The gases to be analyzed are converted catalytically on the solid electrolyte, so that only the gases corresponding to the thermodynamic equilibrium are detected by the reference electrode, or the solid electrolyte converts only the gases interfering with the reference signal.

According to another alternative exemplary embodiment one or more measuring electrodes in addition to the solid electrolyte are designed as porous electrodes, thereby facilitating gas diffusion to the reference electrode.

Compounds of the general formula $AB_2O_6$, i.e., compounds from the class of eschynites, samarskites and euxenites, are used as the measuring electrode materials according to the present invention. All three classes of compounds are subsumed below under the term "eschynites". They have a high specific sensitivity for saturated and unsaturated hydrocarbons in particular. This is increased by partially replacing the B position with a transition metal.

One exemplary embodiment of this class of compounds is $SmTiNi_{0.03}Nb_{1.1}O_6$. Instead of nickel, it is also possible to use platinum, palladium or coinage metals for doping. This doping increases the sensitivity of these eschynites for unsaturated hydrocarbons in particular. $SmTiNi_{0.03}Nb_{1.1}O_6$ is obtained by hydrothermal synthesis.

The high sensitivity of eschynites for unsaturated hydrocarbons in particular is based on adsorptive interactions of the $\pi$ electrons of the double bonds of the corresponding hydrocarbon with electrophilic acceptor sites on the (1,1,0) or (1,1,1) eschynite surface.

The following example describes a method of producing a sensor according to the present invention. $SmTiNi_{0.03}Nb_{1.1}O_6$ produced by hydrothermal synthesis is pressed by a generally known thick-film technique onto a substrate having a reference electrode made of platinum, for example, and above that a solid electrolyte layer composed of stabilized zirconium oxide or hafnium oxide, for example. A heater device is applied to the opposite side of the substrate. The sensor is sintered for 90 minutes at 1200° C. with a heating/cooling ramp of 300° C./h. The solid electrolyte has pores on the order of 10 $\mu$ to 100 $\mu$ in size after sintering. The voltage on the cell constructed in this way is measured at a 1 mΩ resistor between the reference electrode and the eschynite electrode with the help of a printed platinum conductor applied so that it is insulated from the solid electrolyte and contacts only the measuring electrode. The sensor is heated to 600° C. by its heater device.

Figure 2:
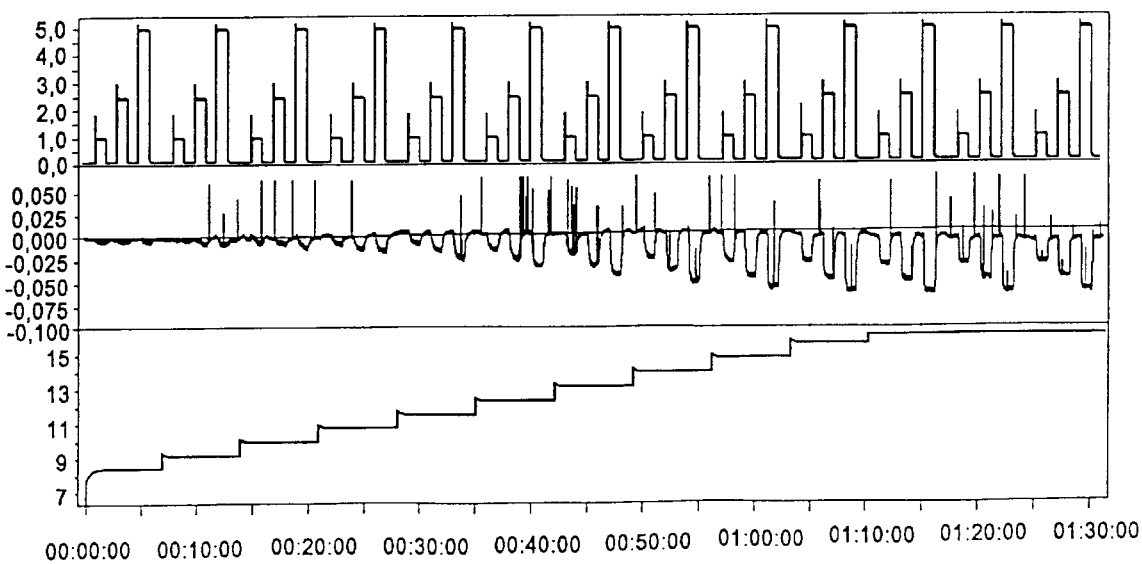
FIG. 2 shows a measured curve of the sensor in detecting a hydrocarbon.

FIG. 2 shows a measured curve of the sensor according to the present invention with eschynite compound $SmTiNi_{0.03}Nb_{1.1}O_6$. The top part of FIG. 2 shows the concentration of the gas to be analyzed, i.e., propane in this case, with oxygen added in the amount of 10 vol %. The value on the ordinate is multiplied by $10^2$ ppm to determine the concentration in ppm. The middle part shows the sensor signal, measured in volts, during a measurement period of one hour and thirty minutes. The bottom part of FIG. 2 shows the increase in heating power, measured in watts.

What is claimed is:

1. A sensor for determining a concentration of oxidizable components in a gas mixture, comprising:
an ion conducting solid electrolyte including at least one reference electrode exposed to a reference atmosphere and at least one measuring electrode exposed to the gas mixture, the at least one measuring electrode composed of a mixed metal oxide according to a general structural formula of:

$$AB_2O_6$$

wherein A includes one of the following: a rare earth metal, Y, La, a heavy alkali metal, an alkaline earth metal, an element from main group III, a naturally occurring actinide, Pb and Bi, and wherein B includes one of the following: a metal from subgroup IV, a metal from subgroup V, Sn, Sb, Re and Fe.

2. The sensor according to claim 1, wherein the sensor detects saturated hydrocarbons and unsaturated hydrocarbons.

3. The sensor according to claim 1, wherein the mixed metal oxide is at least one of synthetically produced and of a natural origin.

4. The sensor according to claim 1, wherein B is at least partially replaced by transition metals, the transition metals including one of platinum metals, coinage metals, iron group metals, rhenium and transition metals in an oxidation state of +5, wherein the transition metals in an oxidation state of +5 are selected from subgroup IV and subgroup V.

5. The sensor according to claim 4, wherein a percentage of substitute ions in B is between 0.005 mol % and 0.2 mol %.

6. The sensor according to claim 1, wherein oxygen of the mixed metal oxide is at least partially replaced or is occupied in excess by at least one of hydroxide anions and fluoride anions.

7. The sensor according to claim 1, wherein at least parts of A have defects.

8. The sensor according to claim 1, wherein a thickness of the at least one measuring electrode is between 5 $\mu$m and 100 $\mu$m.

9. The sensor according to claim 1, wherein a thickness of the at least one measuring electrode is between 20 $\mu$m and 30 $\mu$m.

10. The sensor according to claim 1, wherein the at least one measuring electrode is applied using a thick-film technique.

11. The sensor according to claim 1, wherein the at least one reference electrode and the at least one measuring electrode are arranged in superimposed layers on a surface of a planar, electrically insulating substrate.

12. The sensor according to claim 1, wherein the sensor detects hydrocarbons.

* * * * *

UNITED STATES PATENT AND TRADEMARK OFFICE
CERTIFICATE OF CORRECTION

PATENT NO.   : 6,168,700 B1
DATED        : January 2, 2001
INVENTOR(S)  : Thomas Köhler and Bernd Schumann It is certified that error appears in the above-identified patent and that said Letters Patent is hereby corrected as shown below:

<u>Column 1,</u>
Line 13, change "Formula..." to -- Gas detectors containing sensor materials of the general formula... --

Signed and Sealed this

Fifteenth Day of July, 2003

JAMES E. ROGAN
*Director of the United States Patent and Trademark Office*